United States Patent [19]
Blanco

[11] Patent Number: 4,670,251
[45] Date of Patent: Jun. 2, 1987

[54] MICROCRYSTALLINE TABLETING EXCIPIENT DERIVED FROM WHEY

[75] Inventor: John F. Blanco, West Chester, Pa.

[73] Assignee: Igene Biotechnology, Inc., Columbia, Md.

[21] Appl. No.: 652,685

[22] Filed: Sep. 20, 1984

Related U.S. Application Data

[63] Continuation-in-part of Ser. No. 615,342, May 30, 1984, abandoned.

[51] Int. Cl.$^4$ .................. A61K 7/00; A61K 7/16; A23C 21/00; A23C 21/02
[52] U.S. Cl. .................. 424/465; 524/56; 426/583; 427/3
[58] Field of Search .................. 424/16, 19, 20, 26, 424/34, 35, 36; 524/56; 426/583; 427/2, 3

[56] References Cited

U.S. PATENT DOCUMENTS 3,922,339 11/1975 Shear .................. 424/22
4,036,999 7/1977 Grindstaff .................. 426/549

FOREIGN PATENT DOCUMENTS

80/01104 3/1984 PCT Int'l Appl.

OTHER PUBLICATIONS

Pernarowski, M., PhD, "Solutions, Emulsions and Suspensions", Chapter 83, Remington's Pharmaceutical Sciences (15th Edition, 1975, pp. 1436-1460).
Baichwal, A. R. and Shangraw, Ralph F., "Tableting Properties of a New Protein/Lactose/Mineral Complex", Pharmaceutical Technology, (Sep. 1985).

Primary Examiner—Morton Foelak
Assistant Examiner—Nathan M. Nutter
Attorney, Agent, or Firm—James C. Haight

[57] ABSTRACT

A solid pharmaceutical composition suitable for oral or rectal administration comprising a unit dosage of a pharmaceutically active ingredient (and optionally one or more inert fillers) homogeneously dispersed in a pharmaceutically acceptable binder, wherein at least a major portion (i.e., at least 50% by weight) of the binder is a microcrystalline solid phase prepared by raising the pH of a dairy whey lactose permeate having a pH below about 7 to a pH between about 8 and 10 to form (i) a lactose-rich aqueous solute phase capable of being autoclaved for 10-20 minutes at 121° C. and 15 psi to form a clear, light-colored solute having a pH of about 7; and (ii) a microcrystalline solid phase which contains substantially all of the dissolved solids from said solute phase which would form a precipitate upon autoclaving said solid phase; separating the microcrystalline solid phase from the solute phase; and drying the separated microcrystalline solid phase to form a nontoxic, tasteless, odorless, chalky white free-flowing powder.

25 Claims, 18 Drawing Figures

FIG. 18

* 0.5% Mg.St; blending time 5 min.

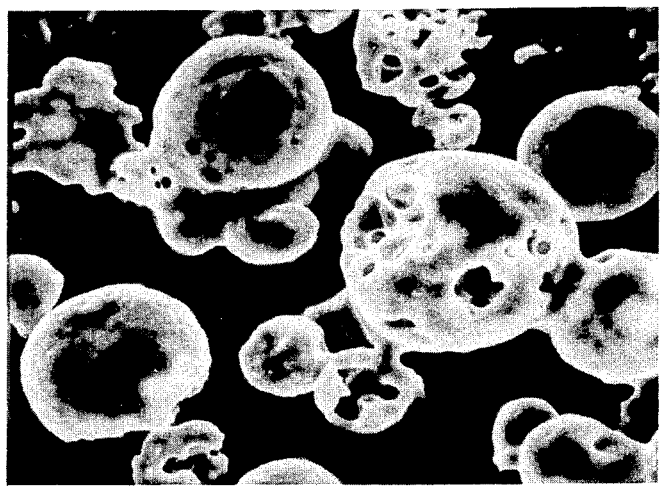
I 15KV 30μM 02.002  FIG. 18
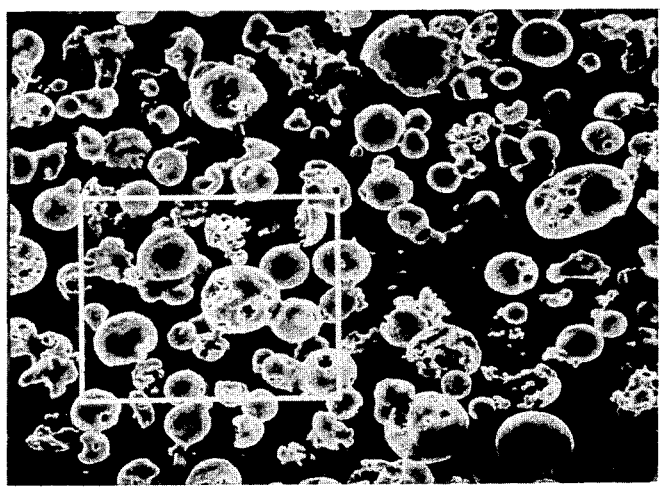
I 15KV 30μM 02.001  FIG. 17

MICROCRYSTALLINE TABLETING EXCIPIENT DERIVED FROM WHEY

DESCRIPTION OF THE INVENTION

1. Cross Reference to Related Application

This is a continuation-in-part of copending, commonly assigned U.S. patent application Ser. No. 06/615,342 filed May 30, 1984 and now abandoned, the contents of which are incorporated by reference herein.

2. Technical Field of the Invention

This invention relates to a new use for a microcrystalline material obtained from dairy whey. More particularly, this invention relates to the unique use of such materials as a binder in either wet or dry granulation formulations, especially in the prepraration of tablets as commonly used in the pharmaceutical industry.

3. Background Art

Binder materials are widely used in the tableting industry for wet granulation, direct compression, and slug (dry granulation) tableting techniques well-known in the art. One widely used material is microcrystalline cellulose of the type sold by FMC Corporation under the Trademark Avicel and described by Orlando Battista, et al. in U.S. Pat. No. 2,978,446 and in Battista U.S. Pat. No. 3,146,168, the contents of which are incorporated by reference herein.

It is well-known that drug substances and pharmaceuticals (as defined in the Federal Food, Drug and Cosmetic Act) are most frequently administered for ingestion (either orally or rectally) in solid dosage forms such as tablets and capsules. Tablets, which may be defined as solid pharmaceutical dosage forms containing drug substances with or without suitable diluents, can be prepared either by compression or molding methods. Compressed tablets are formed by compression and contain no special coating, and can be made from powdered, crystalline, or granular materials, (optionally with a liquid pharmaceutically active material thereon adsorbed or absorbed), either along or in combination with binders, disintegrators, lubricants, diluents, flavoring agents, and colorants. The three general methods of tablet preparation include the wet-granulation method; the dry-granulation method; and direct compression. The physical characteristics of the tableting formation must be such as to allow rapid compression of the tablets and formation of a final product having suitable hardness, disintegration ability, and uniformity, as well as providing availability of the active ingredient and therapeutic efficacy of the dosage form.

Additives which help to impart satisfactory compression characteristics to a tableting formulation include diluents, binders, and lubricants. Diluents are employed when a single dose of the active ingredient is small, and comprise an inert substance to increase the bulk and make the tablet of a practical size for compression. Such diluents are well-known, and can include sugars which impart properties permitting disintegration in the mouth by chewing to form "chewable tablets", as well as non-chewable tablets, e.g. USP lactose, dextrose, calcium sulfate, calcium carbonate, etc.

Binders or granulators are used to impart cohesive qualities to the powdered material and insure that the tablet remains intact after compression, as well as improving the free-flowing qualities by the formulation of granules having a desired hardness and size. Materials commonly used as binders are almost always pre-granulated and include starch, gelatin, sucrose, glucose, dextrose, molasses, and lactose. Natural and synthetic gums have also been used, including acacia, sodium alginate, carboxymethylcellulose, methylcellulose, polyvinylpyrrolidone, etc. Under certain circumstances, materials such as polyethylene glycol, ethylcellulose, waxes, water and alcohol may be considered as binders. The quality and quantity of binder has a considerable influence on the physical characteristics of the compressed tablets. The use of too much binder or too strong a binder forms a hard tablet which will not disintegrate satisfactorily and will cause excessive wear of punches and dyes employed during manufacturing.

The direct compression method for preparing tablets requires a material which is not only free-flowing but is also sufficiently cohesive to act as a binder. Such materials include microcrystalline cellulose, microcrystalline dextrose, amylose, and polyvinylpyrrolidone and the special granulated, crystallized or spray dried forms of many substances, e.g. lactose, sucrose, cellulose, etc.

Compressed tablets must exhibit a suitable tablet hardness or resistance to chipping, abrasion, or breaking under storage, transportation, and handling before usage; if a tablet is too hard, it may not disintegrate in the required period of time, whereas if it is too soft, it will not withstand handling during packaging and shipping. Similarly, the thickness of tablets must be carefully controlled for reproducing tablets identical in appearance and insuring that each production lot will be usable with selected packaging components. Tablet weight tolerances are also important, representing the quantity of granulation which contains the prescribed amount of a therapeutic ingredient. The official compendia also include a content uniformity test in order to insure that every tablet contains the amount of drug substance intended with little variation among tablets within a batch.

Finally, since the in vitro tablet disintegration test does not necessarily bear a relationship to the in vivo action of a solid dosage form (the disintegration test measures only the time required for a group of tablets to disintegrate into particles, and does not take into account the fact that the drug substance must be in solution in order to be absorbed). Unless, this test provides a means of control to assure uniformity from batch to batch. Finally, for certain tablets, dissolution must be standardized to assure uniform drug absorption and physiological availability, which are dependent on having the drug substance in the dissolved state.

Several methods are known for tablet preparation, most commonly the wet-granulation method, the dry-granulation (precompression or double-compression) method, and direct compression. In addition, other processes such as spheronization and spray-congealing have been used; see Remington's Pharmaceutical Sciences, 15th Edition (1975), Mack Publishing Co., Easton, PA, Chapter 89, and particularly pages 1583-1596, the contents of which are incorporated by reference herein.

While many criteria for evaluating the suitability of tablets are subjective, several tests and criteria are set forth in the 1980 USP XX (The United States Pharmacopeia) and will be referred to herein. It can be seen that the process for producing uniform tablets which are storage stable and sufficiently hard and non-friable to resist damage during shipment, yet possess good content uniformity (USP XX Chapter 681) and a satisfactory index of bio-availability (USP XX Chapter 701 disintegration; Chapter 711 dissolution) is a labor and material-intensive production process in which few binder materials are satisfactory for a wide variety of applications.

A far wider variety of materials are known to be suitable as excipients, due to their emulsifying and/or suspending agent properties. However, such materials generally lack the binding capability, flowability, compression properties, and other characteristics to render them suitable for a tableting binder. For this reason, it has become customary to use special direct compression binders in the direct compression process and different binders in the wet and dry phases of the wet-granulation method.

International Patent Publication No. WO 84/01104 of IGI Biotechnology, Inc. published Mar. 29, 1984, the contents of which are incorporated by reference herein, describes a method for treating dairy whey lactose permeate to form a microbiological culture medium and a precipitate which is useful as a good grade additive to cause clouding, stabilization, emulsification, and thickening of food, pharmaceutical, cosmetic, and other compositions. Briefly, a whey ultrafiltration permeate is adjusted to pH 8-10 to form a microcrystalline solids fraction, which is removed by centrifugation and/or ultrafiltration and further processed to form emulsions, gels, or suspensions. In accordance with the present invention, it has now been found that this microcrystalline solids precipitate possesses the unique property of providing binding functionality in both wet and dry granulation processes, in contradistinction to prior art excipients which are typically useful in either wet or dry processes, but not both.

In accordance with the present invention, it has been found that the microcrystalline solids material is useful in size enlargement, agglomeration, or binding of chemical materials, with or without pregelatinized starch, gums, or other inert binders, which is particularly suitable for wet granulation and direct compression tableting processes.

DISCLOSURE OF THE INVENTION

It is a general object of the present invention to provide an inexpensive binder for use in tableting procedures, especially in the pharmaceutical industry.

In is a principal object of the present invention to provide a new binder material with unique properties in that it provides binding properties in both wet and dry compression tableting procedures.

A further object of the present invention is to provide such a binding material which can be used in both the wet and dry stages of the well-known wet-granulation method for preparing tablets.

Another object of this invention is to provides binder materials which are suitable for use in direct compression and slugging process for making tablets.

Yet another object of this invention is to provide novel compositions of matter, particularly pharmaceutical compositions, employing a novel binder material.

BRIEF DESCRIPTION OF THE DRAWINGS

Other objects, features, and advantages of the present invention will become more fully apparent to those skilled in the art to which this invention pertains from the following detailed description, taken in conjunction with the annexed drawings, wherein:

FIG. 17 is a scanning electron micrograph (SEM) of microcrystalline solids fraction showing the typical structure of its particles; and FIG. 18 is an enlarged detailed view taken from the boxed area of FIG. 17 to illustrate the porous, generally hollow sphere structure thereof.

BEST MODE FOR CARRYING OUT THE INVENTION

Figure 1:
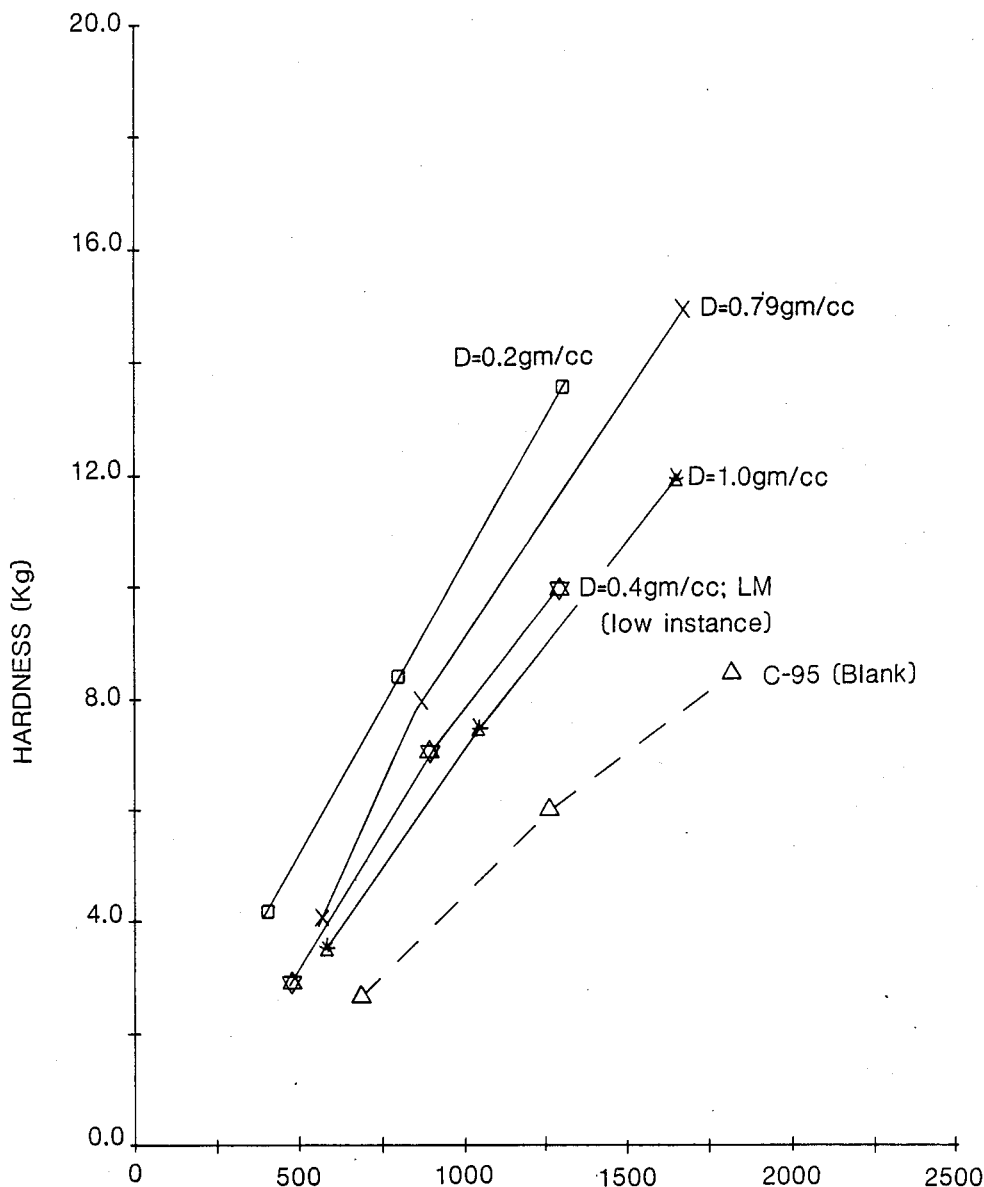
FIG. 1 illustrates the effects of density and moisture content on the compressibility of MWSF prepared according to the methods of Example 1 in terms of hardness vs. compression force.
Figure 2:
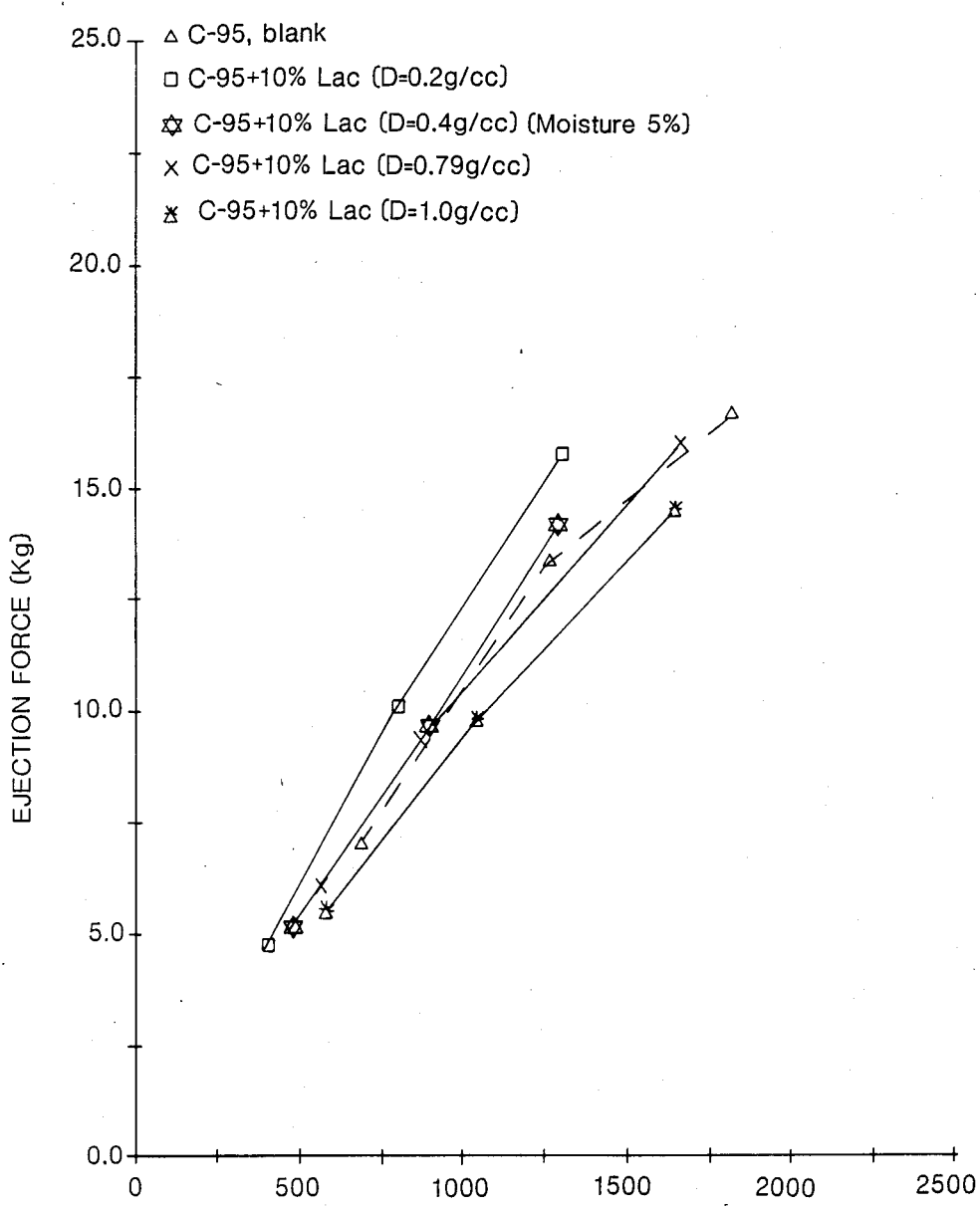
FIG. 2 shows the effects of density and moisture content on the ejection forces required in tableting procedures using MWSF.

Briefly, the above and other objects, features, and advantages of the present invention are attained in one aspect thereof by providing a solid pharmaceutical composition suitable for oral or rectal administration comprising a unit dosage of a pharmaceutically active ingredient (and optionally one or more inert fillers) homogeneously dispersed in a pharmaceutically acceptable binder, wherein at least a major portion (i.e., at least 50% by weight) of the binder is a microcrystalline solid phase prepared by raising the pH of a dairy whey lactose permeate having a pH below about 7 to a pH between about 8 and 10 to form: (i) a lactose-rich aqueous solute phase capable of being autoclaved for 10-20 minutes at 121° C. and 15 psi to form a clear, light-colored solute having a pH of about 7; and (ii) a microcrystalline solid phase which contains substantially all of the dissolved solids from said solute phase which would form a precipitate upon autoclaving said solid phase; separating the microcrystalline solid phase from the solute phase; and drying the separated microcrystalline solid phase to form a nontoxic, tasteless, odorless, chalky white free-flowing powder.

The microcrystalline whey solids fraction (MWSF) is prepared according to the process described in the aforementioned patent application of IGI Biotechnology, Inc., preferably by raising the pH of diluted whey lactose permeate to about 9 to form the precipitate and physically separating the precipitate by centrifugation and ultrafiltration, e.g., across a 20–100 kdal molecular weight exclusion membrane.

Presently preferred applications are those wherein the active ingredient is a flavoring agent and the resultant tablet is a confectionery, especially a candy; the active ingredient is a bakery dough conditioner or modifier and the resultant tablet is a unit dosage form of said ingredient; the active ingredient is a pharmaceutical; the active ingredient is a vitamin; and/or the active ingredient is a dietary mineral supplement. Presently preferred characteristics of the microcrystalline solid phase are those wherein the microcrystalline solid phase comprises a major portion of generally spherical, partially porous particles about 5–100 microns in diameter; optionally wherein said particles are agglomerated to form flowable granules; and wherein the particles are typified by the structure shown in FIG. 9.

It has now been found that the use of water rather than a lower alkanol in wet granulation processes using the microcrystalline solids fraction according to the present invention is generally preferred when maximum agglomeration properties are desired, since these properties have been observed to decrease when an alcohol rather than water is used.

For most applications, the microcrystalline solids fraction generally has a density of 0.2–1.0 g/cc, preferably about 0.5–0.8 g/cc, and especially about 0.6 g/cc. Among samples having equal moisture content, flow properties decrease due to smaller particle sizes at densities below about 0.5 g/cc and flow properties increase but with some loss in compressibility at densities above about 0.8 g/cc, although still satisfactory for tableting use.

As a dry binder MWSF can be used at a 10 to 15% concentration in a free flowing formulation and about 20% with a high dose active possessing low compressibility. The only disadvantage is the slight stickiness directly related to the concentration present.

As an in-situ binder in wet granulation, water appears to be the best solvent and at a 7.5% level it forms tablets which are comparable to the tablets formed with other commonly used in-situ binders. It is not nearly as effective when granulated with hydroalcoholic solutions. Based on this evaluation, MWSF has properties both as a dry binder and an in-situ binder in wet granulation.

Considerable work needs to be done in optimizing the physical and possibly the chemical properties of MWSF for tableting purposes. The major physical disadvantage at this time appears to be the stickiness of the powder when handled in the presence of high humidity and the sticky nature imparted to tablet surfaces.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all pressures are ambient and all parts and percentages are by weight.

EXAMPLE 1

Direct Compression

Microcrystalline solids fraction (Lactomin TM IGI Biotechnology, Inc., Columbia, MD, 10% w/w) was compared to microcrystalline cellulose (Avicel PH-101 ® 1244, FMC Corporation, Philadelphia, PA, MCC, 10% w/w), a commonly used unique dry binder, in three kinds of formulations.

1. Vit C (C-95 ®), Roche Chemical Division, Hoffman-LaRoche, Inc., Nutley, NJ) a free-flowing directly compressible product
2. Unmilled dicalcium phosphate (Di-Tab ®, Stauffer Chemical Co., Westport, CT) representing a water insoluble formulation, and
3. Compressible sugar, a water soluble product (Di-Pac ®, Amstar Corp., New York, NY).

Ac-Di-Sol ® T245 (FMC Corporation, Philadelphia, PA, 2% w/w) was used as a disintegrant and magnesium stearate NF (Mallinckrodt, Inc., St. Louis, MO, 0.5% w/w) was used as a lubricant. The exact compositions of the six directly compressible formulations are given in Table 1.

TABLE 1

| COMPOSITION OF DIRECT COMPRESSION FORMULATIONS | | | | | | |
|---|---|---|---|---|---|---|
| | FORMULATIONS IN PARTS BY WEIGHT | | | | | |
| MATERIALS | I | II | III | IV | V | VI |
| Vit C, C-95 | 87.50 | 87.50 | -.- | -.- | -.- | -.- |
| UNMILLED DCP | -.- | -.- | 87.50 | 87.50 | -.- | -.- |
| COMPRESSIBLE SUGAR | -.- | -.- | -.- | -.- | 87.50 | 87.50 |
| MICROCRYSTALLINE SOLIDS FRACTION | 10.00 | -.- | 10.00 | -.- | 10.00 | -.- |
| MCC | -.- | 10.00 | -.- | 10.00 | -.- | 10.00 |
| Ac-Di-Sol(R) | 2.00 | 2.00 | 2.00 | 2.00 | 2.00 | 2.00 |
| MAGNESIUM STEARATE | 0.50 | 0.50 | 0.50 | 0.50 | 0.50 | 0.50 |

500 batches were prepared by mixing the ingredients (except magnesium stearate) in a two quart PK blender for five minutes. Magnesium stearate was then added to the above mix and further blended for an additional five minutes. Tablets were compressed on an instrumented RB-2 Stokes rotary press using 7/16" flat-faced tooling to a constant thickness value of 0.115"±0.005". Compression and ejection forces were monitored while compressing.

Tablets were stored in screw capped glass bottles and evaluated after at least 24 hours for hardness on an Erweka TAH28 Hardness Tester.

Figure 3:
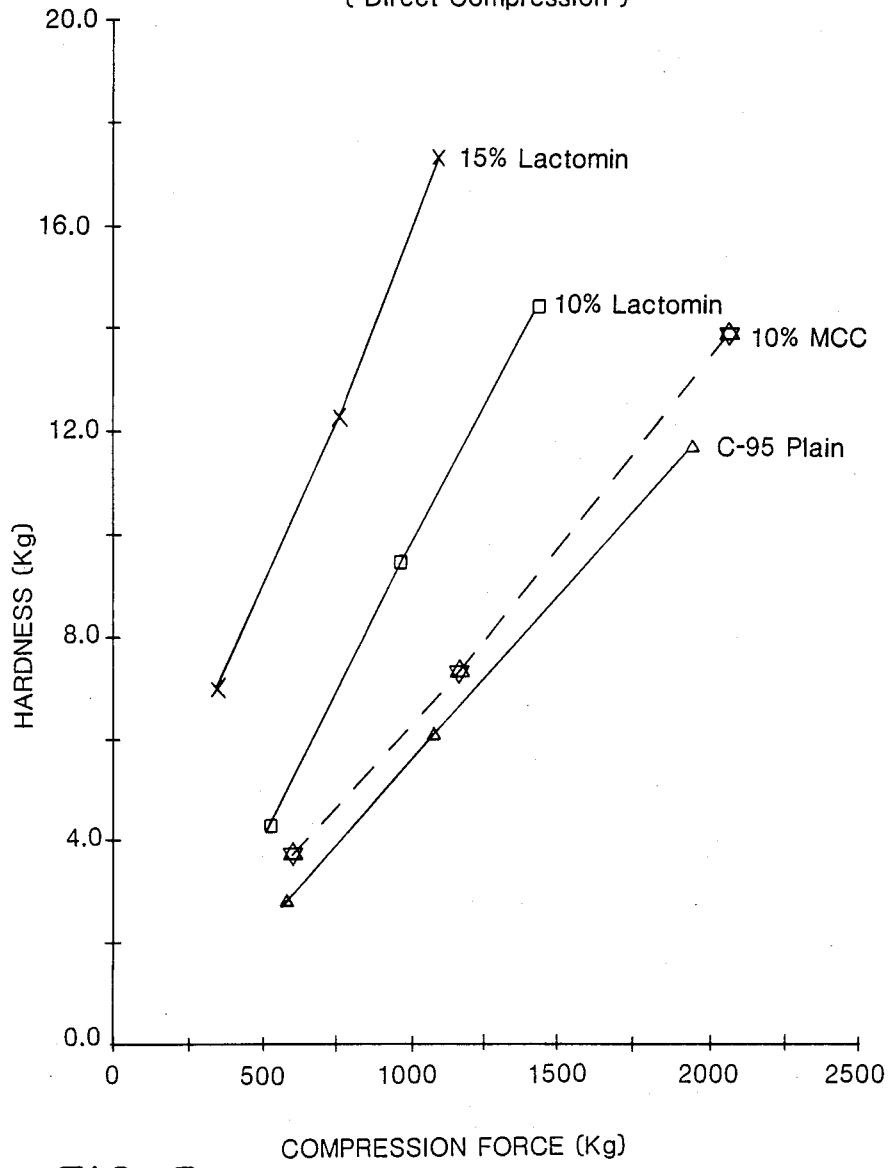
FIG. 3 illustrates the dry binding of microcrystalline solids fraction in comparison with the current industry standard microcrystalline cellulose (Avicel, trademark of FMC Corporation) showing that the MWSF provides much harder tablets at lower compression forces.

At equivalent compression forces microcrystalline solids fraction formed harder Vit. C tablets than microcrystalline cellulose as is shown in FIG. 3. The difference in hardness values between the two formulations increased with increasing compression force and at about 1,500 kg microcrystalline solids fraction based tablets were 50% stronger than microcrystalline cellulose based tablets.

Figure 4:
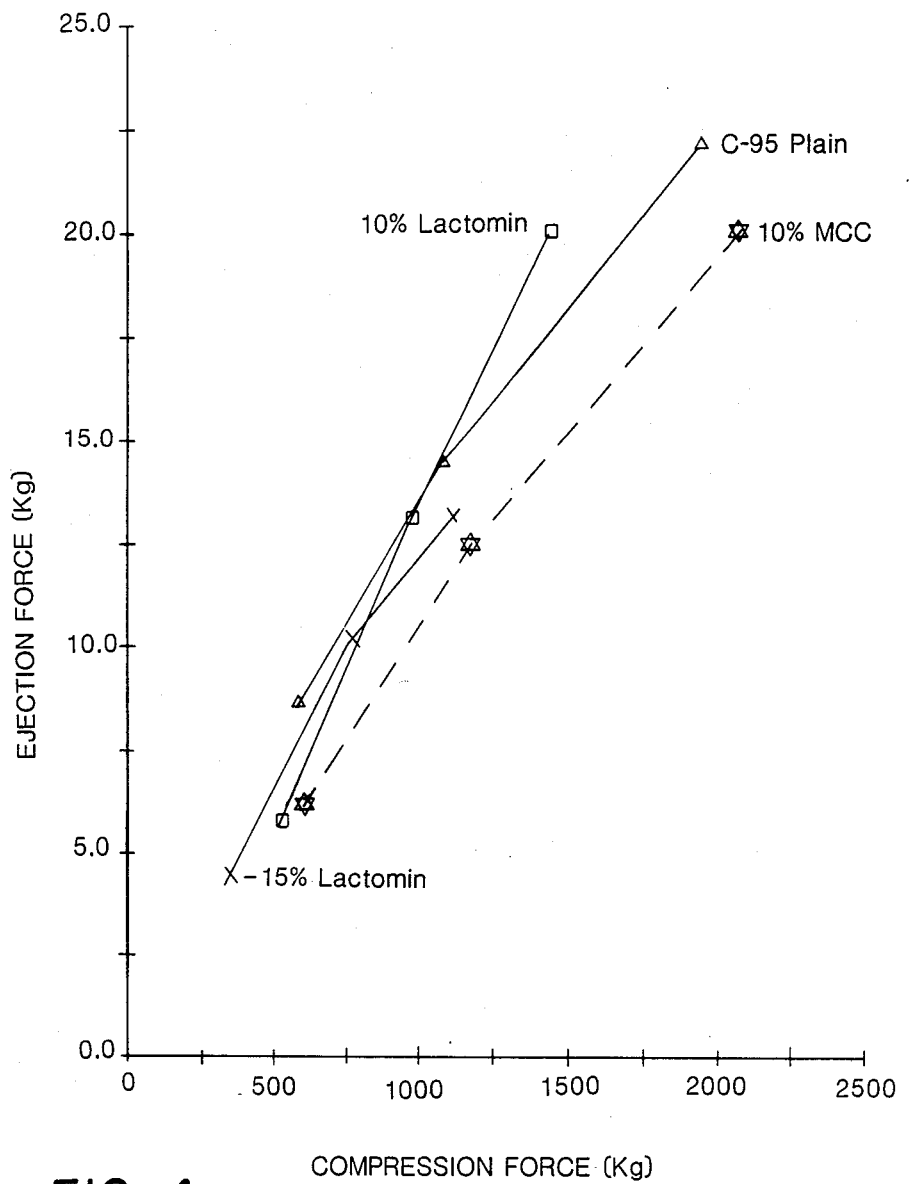
FIG. 4 shows that the tablets made with the microcrystalline solids binder are easily released from the tablet press.

In the same formulation, microcrystalline solids fraction exhibited higher ejection forces than microcrystalline cellulose as shown in FIG. 4. The difference between the two also increased at higher compression forces. This demonstrates that microcrystalline solids fraction based formulations may need higher levels of lubricant (>0.5%).

Figure 5:
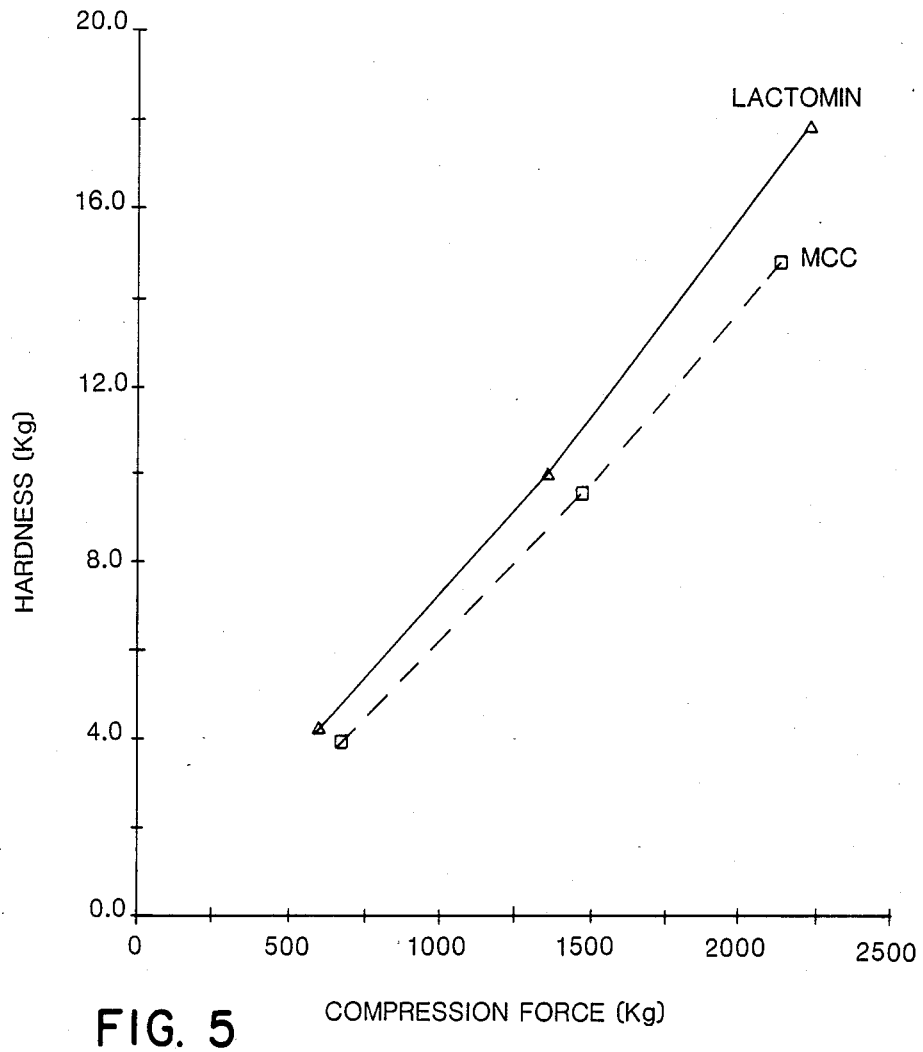
FIG. 5 shows the improved compressibility of dicalcium phosphate (an insoluble filler) when used with microcrystalline solids fraction as a binder in comparison to microcrystalline cellulose.
Figure 6:
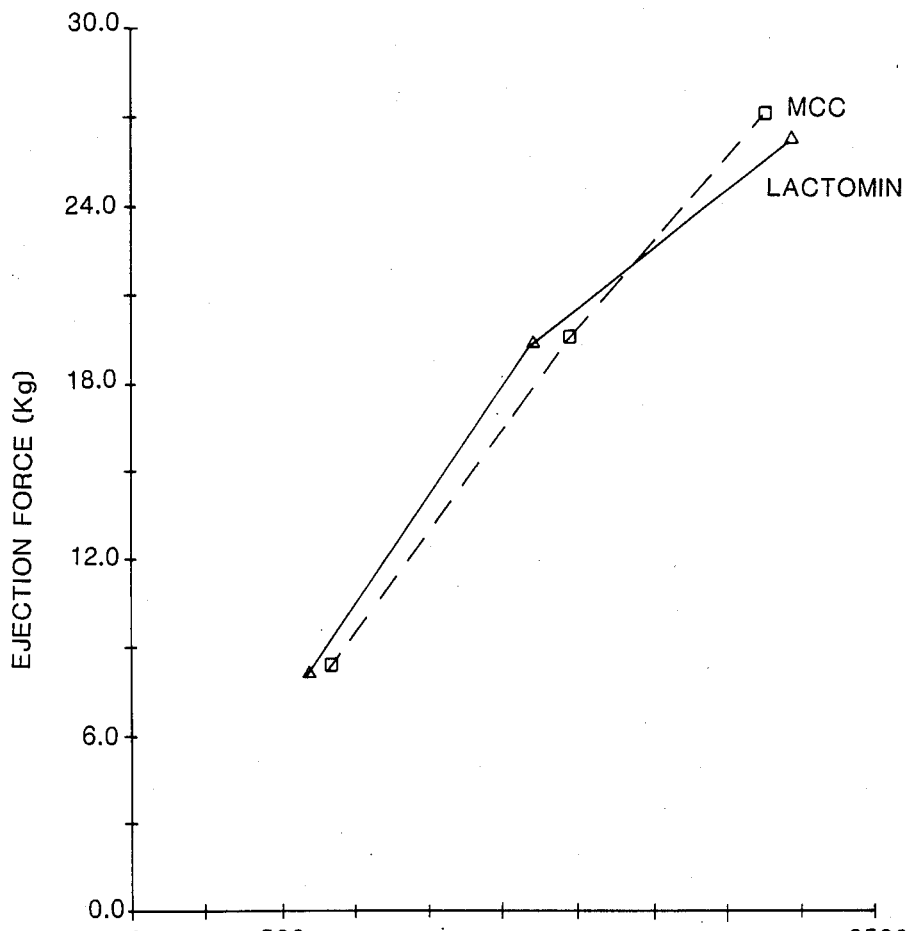
FIG. 6 shows essentially identical compression/ejection forces of the material illustrated in FIG. 5.

The dicalcium phosphate based formulation also showed better compressibility with microcrystalline solids fraction as a dry binder when compared to microcrystalline cellulose, as seen in FIG. 5. Here the compressibility profiles are almost parallel. The ejection force profiles for these two formulations is shown in FIG. 6 and indicates almost no difference between the two profiles.

Figure 7:
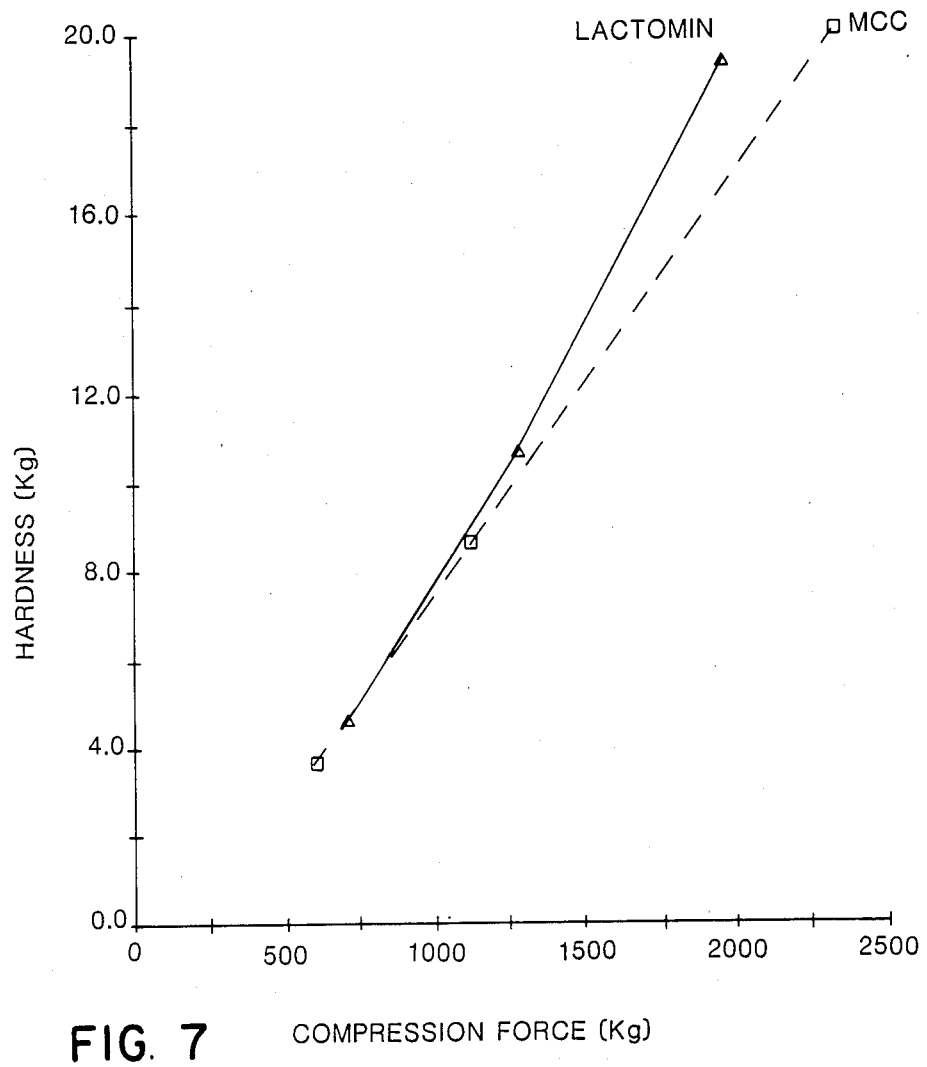
FIG. 7 shows the increased hardness of sugar tablets using microcrystalline solids as a binder.
Figure 8:
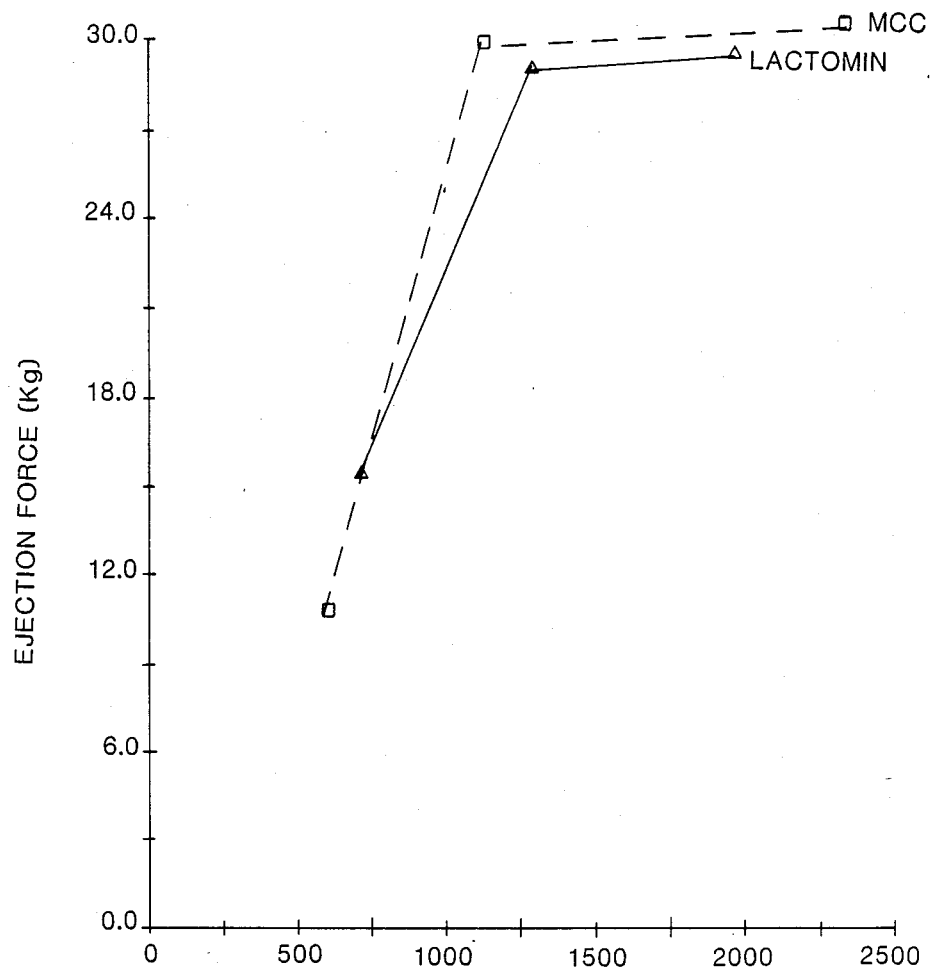
FIG. 8 shows essentially no difference in the lubricant requirements of the compositions illustrated in FIG. 7.

Microcrystalline cellulose traditionally does not significantly improve the compressibility of compressible sugar. As seen in FIG. 7, microcrystalline solids fraction again performs slightly better than microcrystalline cellulose, particularly at higher compression forces. The ejection force profiles for both materials in the compressible sugar formulations were similar and both exhibited a plateau effect after a sharp increase as depicted in FIG. 8.

Based on the above data, microcrystalline solids fraction appears to be superior or equal to microcrystalline cellulose at a 10% w/w level in otherwise identical formulations with the other directly compressible materials used in this example.

EXAMPLE 2

Optimizing the level of MWSE in Direct Compression (a)

Vit C; C-95 which is a free-flowing directly compressible product was used for this purpose and MWSF concentrations of 0% and 15% were compared to the data of Example 1 for 10% Lactomin where a 10% microcrystalline cellulose formulation was also used as standard. The composition of the formulation is given below; the tableting procedure was the same as described in Example 1.

|  | % w/w | % w/w |
|---|---|---|
| Vit. C, C-95 | 97.5 | 82.5 |
| Lactomin | — | 15.0 |
| Ac-Di-Sol | 2.0 | 2.0 |
| Magnesium Stearate | 0.5 | 0.5 |
|  | 100.0 | 100.0 |

Increasing the amounts of MWSF dramatically increased the compressibility of the formulation as can be seen in FIG. 3. Addition of 10% MWSF provided 50% stronger tablets than without MWSF at equivalent compression forces. Increasing the MWSF concentration to 15% further increased the compressibility of an additional 50%. As compared to MWSF, microcrystalline cellulose at similar concentrations only slightly increases the compressibility of C-95.

MWSF based formulations showed slightly higher ejection forces than microcrystalline cellulose based formulations. The addition of microcrystalline cellulose in fact lowered the ejection forces when compared to plain C-95 in FIG. 4. The 15% MWSF based formulation showed some sticking and picking while all the other formulations including the plain C-95 caused a slight filming of the punches.

(b)

The model non-compressible high dose drug used in this part of the study initially was Vit-C (crystals) but due to excessive sticking and picking it was decided to use acetaminophen dense powder (Malinckrodt, Inc.) instead. The formulation which produced reasonably acceptable tablets was studied and is shown below.

|  | % w/w |
|---|---|
| 1. Acetaminophen | 78.80 |
| 2. MWSF/M.C.C. | 20.00 |
| 3. Zeolex | 0.20 |
| 4. Magnesium Stearate | 1.00 |
|  | 100.00 |

The first three ingredients were blended for 5 minutes in a two-quart P.K. blender and further blended for 10 minutes after addition of magnesium stearate. The target weight of the tablets was adjusted such that each tablet contained 325 mg of acetaminophen (5 mg overage) as active ingredient. A similar formulation with 20% microcrystalline cellulose was also prepared as a control.

Figure 9:
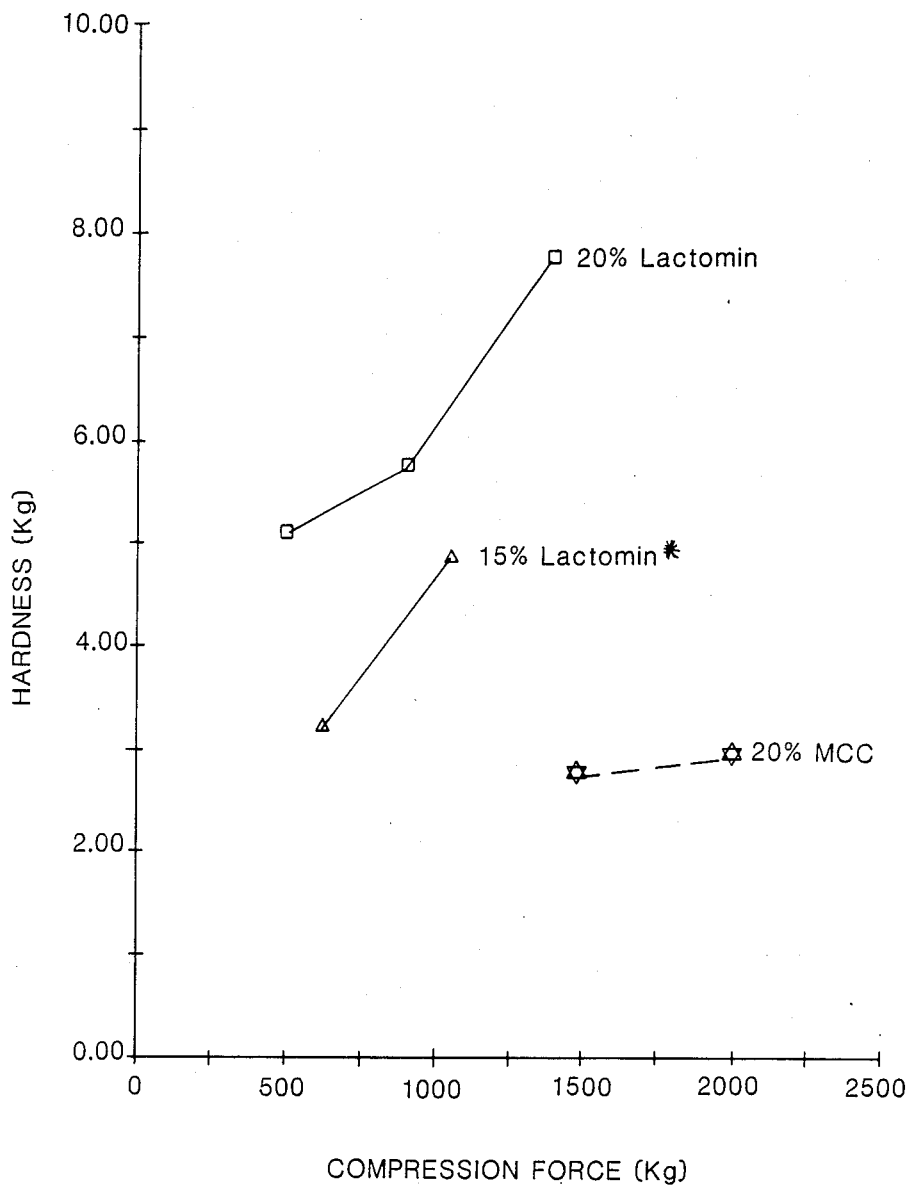
FIG. 9 shows the improved compressibility of acetaminophen formulations when used with microcrystalline solids fraction as a binder in comparison to microcrystalline cellulose.
Figure 10:
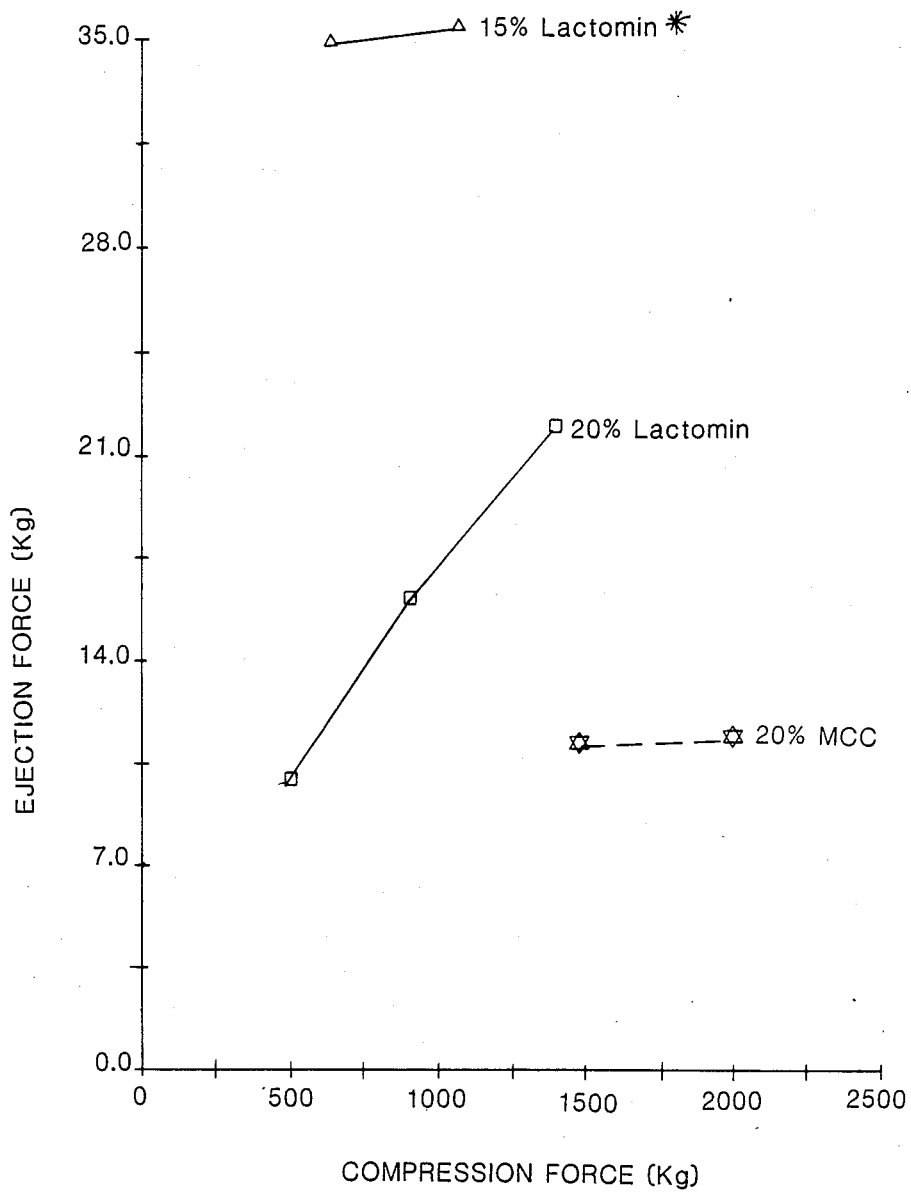
FIG. 10 shows the compression/ejection forces of the material illustrated in FIG. 9.

Acetaminophen tablets of around 6 to 8 kg hardness at a compression force of 1000 to 1500 kg could be formed using 20% MWSF. Similar tablets with 20% microcrystalline cellulose were friable and had hardness values between 2 and 3 kg at a compression force range of 1500 to 2000 kg as shown in FIG. 9. The 15% MWSF formulation contained only 0.5% magnesium stearate as a lubricant, which resulted in very high ejection forces as shown in FIG. 10. Therefore, the lubricant level was increased to 1% and blending conducted for 10 minutes. Tablets containing MWSF still exhibited considerably higher ejection forces than those containing microcrystalline cellulose at a 20% level. In addition, the MWSF tablets were slightly sticky to the touch.

TABLE 2

DISINTEGRATION DATA

| Formulation | Hardness (kg) | D.T. (min.) |
|---|---|---|
| C-95 Plain | 11.56 | 8.95 |
| C-95 + 10% Lactomin | 14.25 | 7.72 |
| C-95 + 15% Lactomin | 12.12 | 7.58 |
| C-95 + 10% M.C.C. | 13.74 | 8.45 |

EXAMPLE 3

Effect of Dry Binders on the Compressibility of Calcium Carbonate Granulations

| FORMULATIONS: | % w/w COMPOSITIONS | | | | | |
|---|---|---|---|---|---|---|
|  | I | II | III | IV | V | VI |
| calcium carbonate (pptd) | 91.00 | 81.00 | 81.00 | — | — | — |
| calcium carbonate (oyster shell) | — | — | — | 91.00 | 81.00 | 81.00 |
| P.V.P. | 5.00 | 5.00 | 5.00 | 5.00 | 5.00 | 5.00 |
| MWSF | — | 10.00 | — | — | 10.00 | — |
| Avicel(R) PH-101 | — | — | 10.00 | — | — | 10.00 |
| Ac-di-sol | 3.00 | 3.00 | 3.00 | 3.00 | 3.00 | 3.00 |
| Magnesium Stearate | 1.00 | 1.00 | 1.00 | 1.00 | 1.00 | 1.00 |

Preparation of base granules:

-continued

| Ingredients | gm/1.5 Kg batch |
| --- | --- |
| calcium carbonate (o.s. or pptd) | 1402.50 |
| PVP (5%) | 75.00 |
| Ac-di-sol (1.5%) | 22.50 |
| | 1500.00 |

The indicated ingredients were weighed and dry blended in a Hobart mixer for 5 minutes. Water was added through a burette and blending continued until the end point in granulation was achieved. The amount of water for calcium carbonate (pptd) to form acceptable granules was 575 ml and a blending time of 50 minutes. Oyster shell calcium carbonate on the other hand needed 375 ml of water and a blending time of 35 minutes to form acceptable granules.

The wet mass was passed through an oscillating granulator with #10 mesh screen and then dried in a hot air oven at 50° C. temperature overnite. The dry granules were passed through the granulator, this time utilizing a #20 mesh screen.

400 gm batches were then prepared by adding other ingredients depending on the formulation (except for the lubricant) along with the granules and blended in a 2-qt. P.K. blender for 5 minutes. To the above mix 1% magnesium stearate was then added and further blended for 5 minutes.

Figure 11:
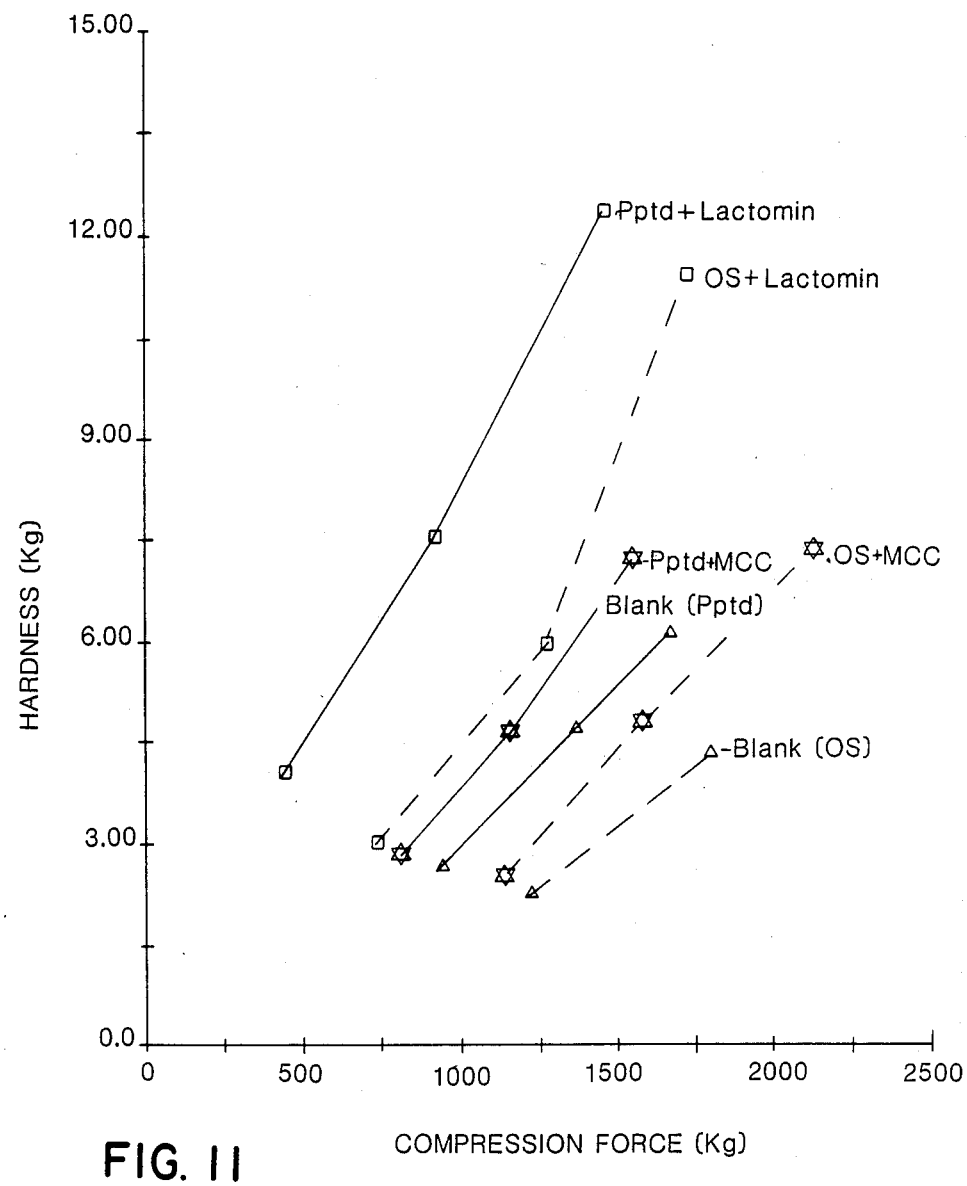
FIG. 11 shows the improved compressibility of two calcium carbonate formulations (precipitated or obtained from oyster shells) when used with microcrystalline solids fraction as a binder in comparison to microcrystalline cellulose.
Figure 12:
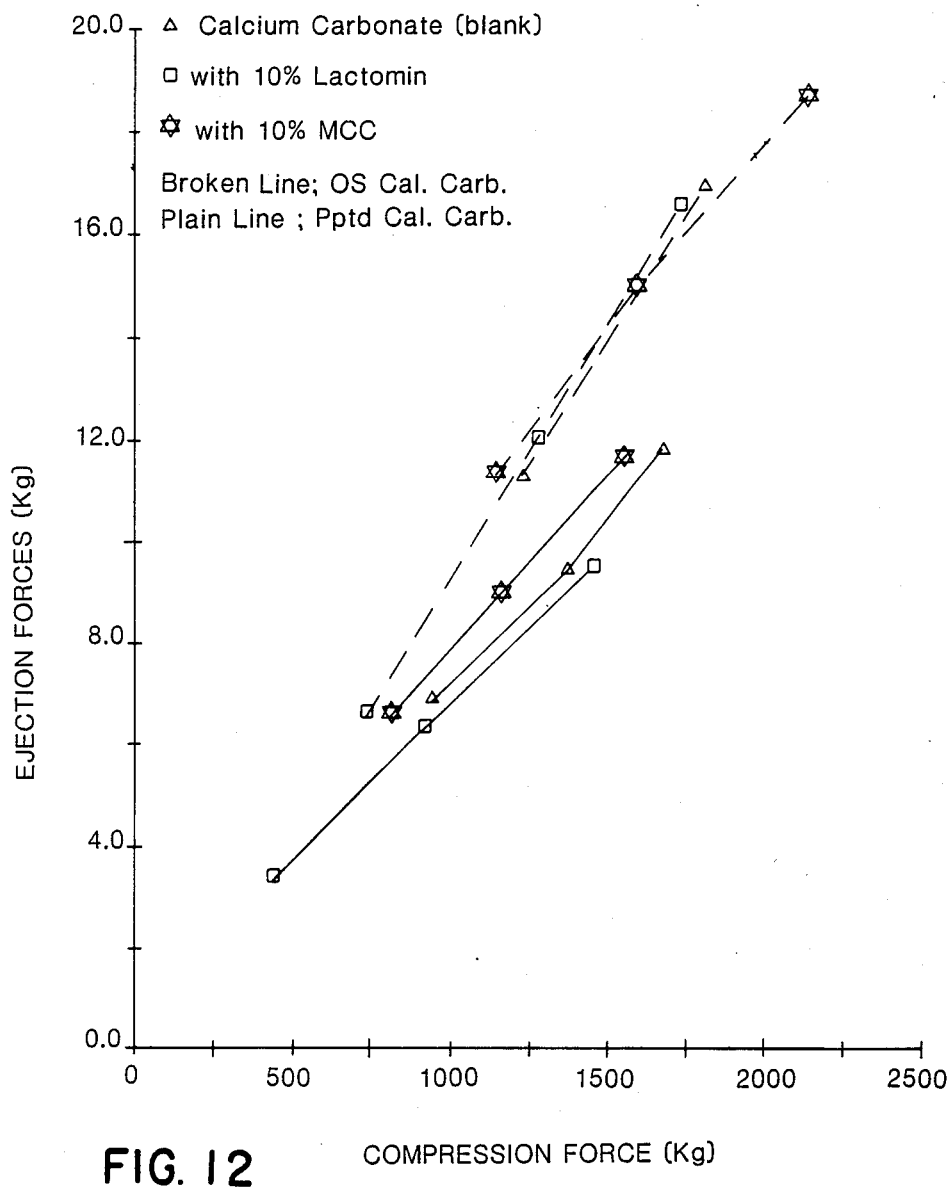
FIG. 12 shows the compression/ejection forces of the material illustrated in FIG. 11.

Tablets were prepared by compressing these formulations on an instrumented rotary RB-2 press with ⅜" flat faced tooling to a constant thickness of 0.125"±0.005". Compressed tablets were stored in screw capped amber bottles and their hardness tested (Erweka TBH-28) after storing the tablets overnite. Data on compression, ejection forces and hardness is presented in FIGS. 11 and 12.

EXAMPLE 4

Wet Granulation

Microcrystalline solids fraction (5% w/w) was compared to polyvinylpyrrolidone (Povidone® USP, G-101, GAF Corporation, New York, NY) and a specialty pregelatinized starch (National 78-1973 NF, National Starch & Chemical Corporation, Bridgewater, NJ, both 5% w/w) which are among the currently best available wet granulating binders. The granulation was made from a 50/50 mix of Milled Dicalcium Phosphate Anhydrous, F130 33R1 (Stauffer Chemical Co., Westport, CT) Lactose Hydrous U.S.P. (SD 127, Foremost-McKesson, Inc., San Francisco, CA), fillers usually used in standard wet granulation formulations. The general formulation is listed below in Table 3:

TABLE 3

COMPOSITION OF WET GRANULATION FORMULATIONS

| | % (w/w) | gm/kg batch |
| --- | --- | --- |
| Dicalcium Phosphate | 45.5 | 455.0 |
| Lactose (Hydrous) | 45.5 | 455.0 |
| Binder (microcrystalline solids fraction/PVP/Preg. Starch) | 5.0 | 50.0 |
| Ac-Di-Sol(R) | 3.0 | 30.0 |
| Magnesium Stearate | 1.0 | 10.0 |
| | 100.0 | 1000.0 |

The fillers, binder and half of the Ac-Di-Sol were blended in a Hobart bowl for five minutes. Water was then added slowly to the bowl through a burette as the powder mass was being mixed. A record was maintained as to the amount of water and also the total time of mixing required to form the wet mass characteristic of the end point in granulation.

The wet mass was screened through a #12 mesh screen and dried on paper lined trays in a hot air oven at 50°-55° C. for 12 hours.

The dried granules were then passed through a #20 mesh screen and the remaining Ac-Di-Sol ® was added and blended in a two quart P.K. blender for three minutes. The appropriate quantity of magnesium stearate was then added to the above granules and was blended for an additional five minutes.

The tableting procedure and evaluation was the same as described in the direct compression Example.

Tablets of similar hardness, hence similar porosities (the thickness was same in all cases) were also evaluated for disintegration time (D.T.) as described in USP XX, Chapter 711. The hardness and disintegration properties are shown in Table 4.

TABLE 4

TABLET DISINTEGRATION DATA

| ACTIVE INGREDIENT | BINDER | TABLETING METHOD | HARDNESS (kg) | D.T. (min) |
| --- | --- | --- | --- | --- |
| C-95 | MICROCRYSTALLINE SOLIDS FRACTION | DIRECT COMPRESSION | 14.27 | 7.72 |
| C-95 | MCC | DIRECT COMPRESSION | 13.74 | 8.45 |
| DICAL PHOS | MICROCRYSTALLINE SOLIDS FRACTION | DIRECT COMPRESSION | 9.84 | 3.47 |
| DICAL PHOS | MCC | DIRECT COMPRESSION | 9.42 | 0.26 |
| COMP. SUGAR | MICROCRYSTALLINE SOLIDS FRACTION | DIRECT COMPRESSION | 19.24 | 4.03 |
| COMP. SUGAR | MCC | DIRECT COMPRESSION | 19.93 | 4.79 |
| 50/50 DICAL PHOS/ LACTOSE HYDROUS | MICROCRYSTALLINE SOLIDS FRACTION | WET GRANULATION | 6.11 | 0.54 |
| 50/50 DICAL PHOS/ LACTOSE HYDROUS | PVP | WET GRANULATION | 7.94 | 1.73 |
| 50/50 DICAL PHOS/ LACTOSE HYDROUS | PREG. STARCH | WET GRANULATION | 8.78 | 0.80 |

The use of microcrystalline solids fraction as an in-situ binder in wet granulation can be justified by the following observations. The amount of water used as solvent was identical (165 ml) in case of both microcrystalline solids fraction and PVP, (optimal for PVP; no attempt was made to optimize the amount of water used to dissolve the microcrystalline solids fraction). On the other hand, the starch required 260 ml of water to form an acceptable mass for granulation. The time required for wet massing was similar, about thirty minutes for all three binders.

Figure 13:
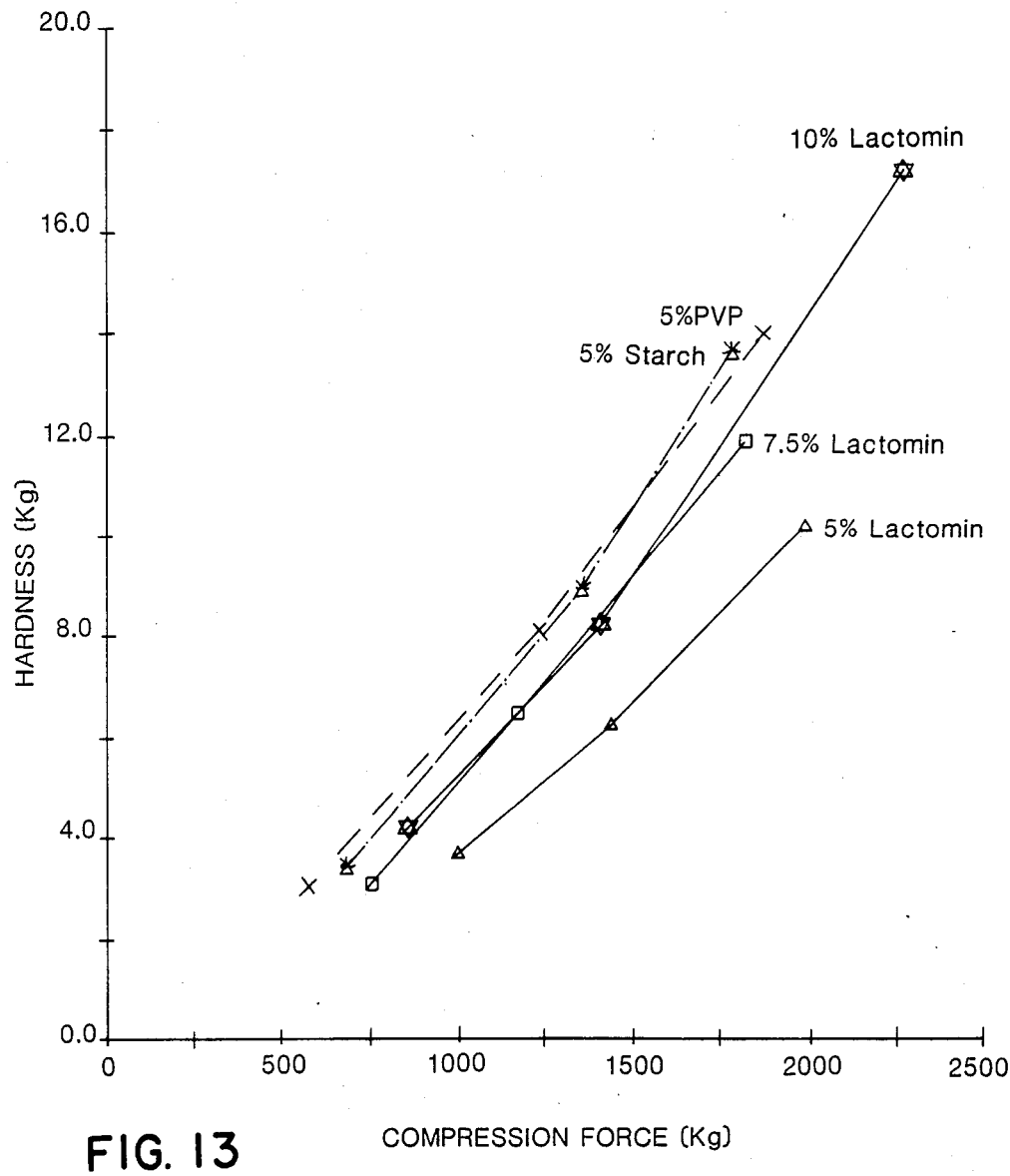
FIG. 13 shows the suitability of microcrystalline solids fraction as a wet binder (a property not shared by pure microcrystalline cellulose preparations currently available)

The compressibility of these three granulations is compared in FIG. 13. While PVP and starch had identical compressibility, microcrystalline solids fraction granules formed softer tablets at identical compression forces. However, microcrystalline solids fraction did make sufficiently hard granules (even at the suboptimal moisture content of 16.5% employed) to form tablets upon compression at 5% and should give comparable hardness with the moisture content increased to optimum level or when the microcrystalline solids content is increased to 8-10% to enhance its wet binding properties.

While a good binder should aid in forming hard tablets, the tablets should readily disintegrate when exposed to the gastro-intestinal fluids, dissolve and release the active ingredient as fast as possible for conventional tablets. A good binder should therefore not hamper this property of the tablet. The data on disintegration in Table 3 shows that microcrystalline solids fraction does not cause this problem and the tablets formed are comparable to the disintegration times of similar tablets made with microcrystalline cellulose.

The level of binder and the amount of solvent were empirically selected based on previous experience with the PVP and pregelatinized starch controls. Variables such as the type and amount of solvent, level of binder, etc. can be varied for microcrystalline solids fraction when used as an in-situ binder in order to optimize its effectiveness.

Figure 14:
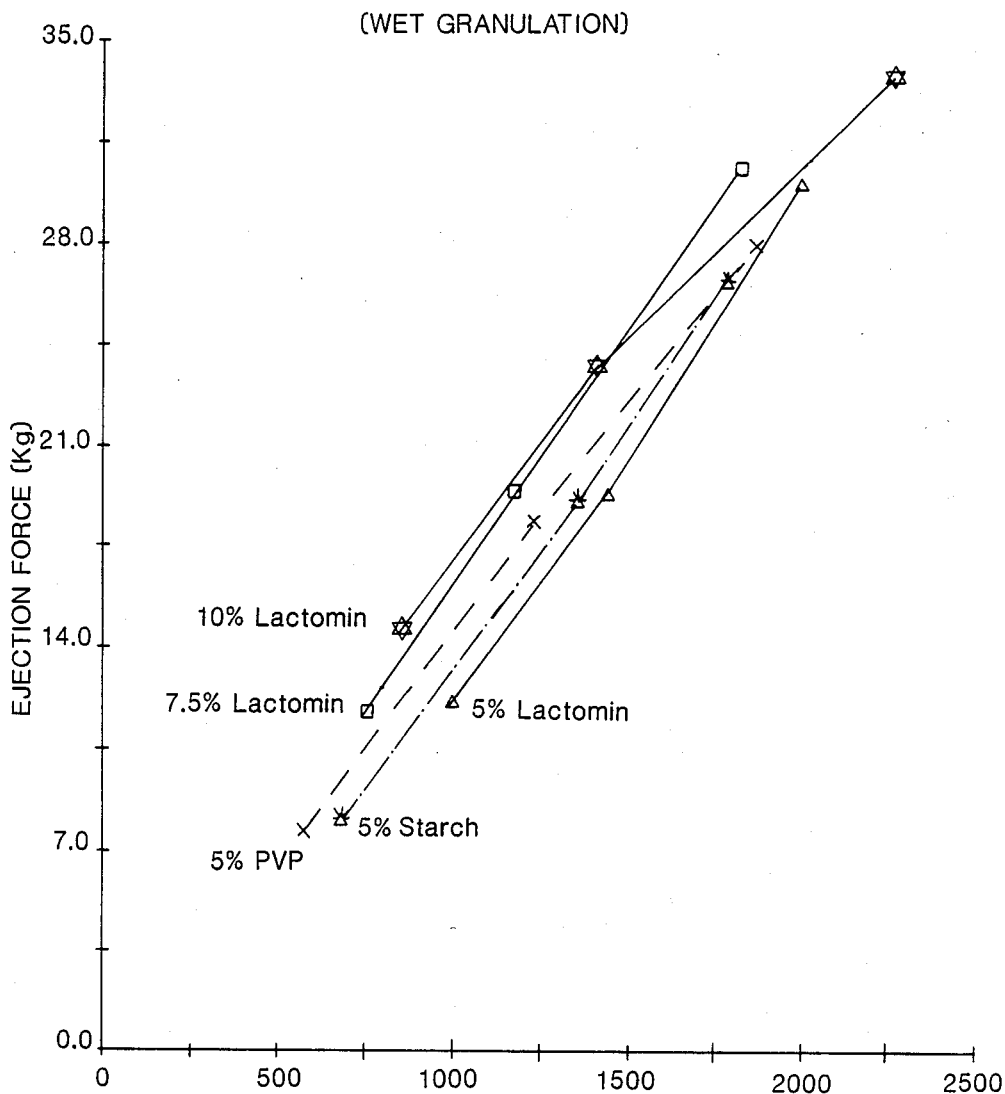
FIG. 14 shows no difference in lubricant requirements for the samples illustrated in FIG. 13.

The ejection forces for the tablets were almost identical, as shown in FIG. 14.

A wet granulation process involves batch operation and many more variables, but the ability of microcrystalline solids fraction to form granules at 5% w/w levels which can be compressed into tablets of about 10 kg hardness at 2000 kg compression force indicates its excellent suitability for use in wet granulation.

EXAMPLE 5

Optimizing the Level of MWSF in Wet Granulation

The standard formulation of 50/50 hydrous lactose/dicalcium phosphate dihydrate was used and MWSF concentrations of 7.5% and 10% were studied using water as a solvent. MWSF was compared to polyvinylpyrollidone at the 7.5% level using a 50/50 hydroalcoholic blend of 95% ethyl alcohol and water as the granulating agent. The procedure used was described in Example 1.

The compressibility profiles of the 50/50 dicalcium phosphate/hydrous lactose wet granulation formulations with different in-situ binders and with different concentrations of MWSF are shown in FIG. 13. Increasing the concentration of MWSF to 7.5% increased the compressibility of the formulation which is comparable to the 5% PVP or starch granulations of Example 4. Addition of 10% MWSF did not prove any more beneficial than 7.5%. The amount of water added in both cases was 200 ml and the blending time around 20 to 30 minutes. In this wet granulation formulation 7.5% MWSF seems to be an optimum concentration as an in-situ binder.

The ejection forces for the 7.5% and 10% MWSF formulations were slightly greater than the 5% MWSF formulations as depicted in FIG. 14. The 5% PVP and starch granulations had ejection forces in between the 5% and 75% or 10% MWSF granulations.

Figure 15:
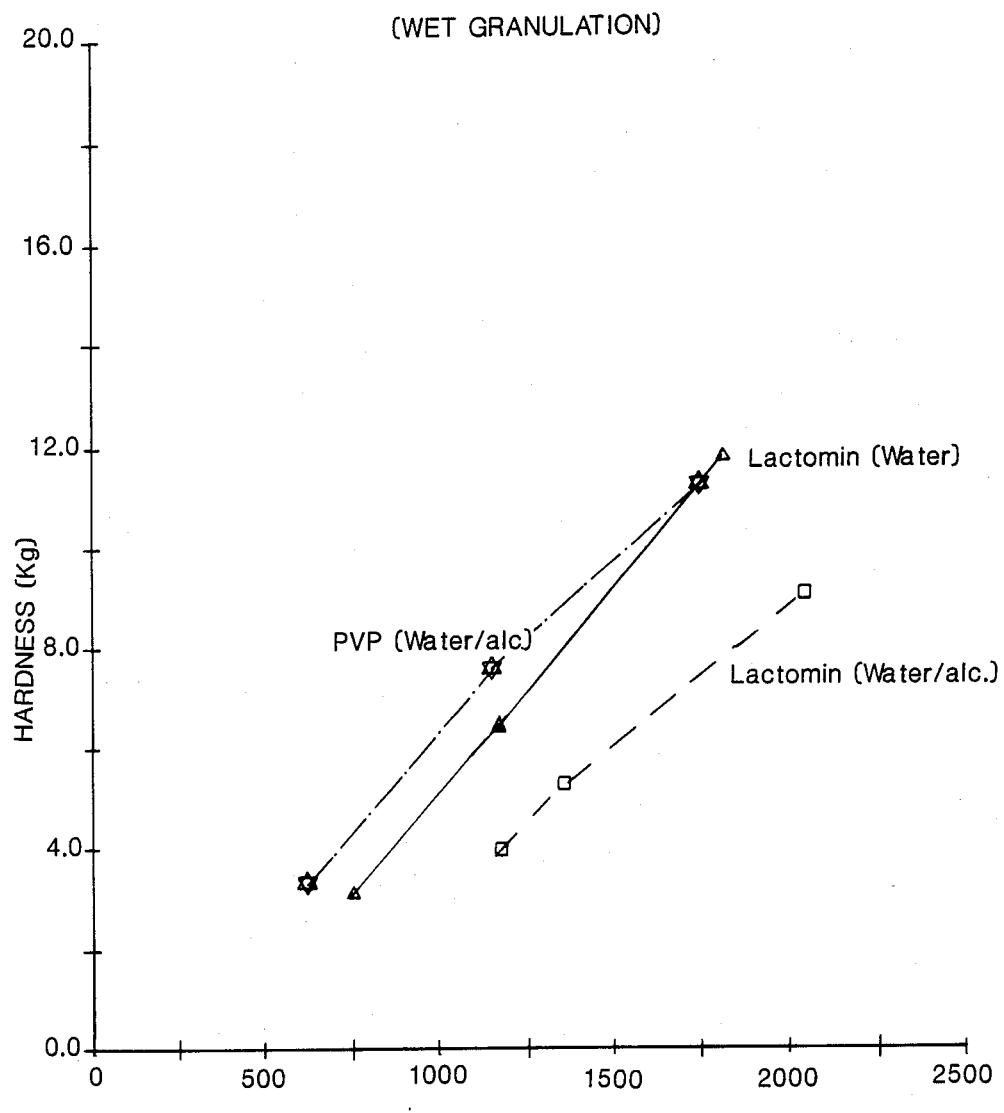
FIG. 15 shows the improved compressibility of two wet granulation formulations (using water or water/alcohol) of dicalcium phosphate and hydrous lactose when used with microcrystalline solids fraction as a binder in comparison to polyvinylpyrrolidone.

The change in solvent from water to a 50/50 hydroalcoholic mixture of solvent reduced the compressibility of the 7.5% MWSF granulation when compared to water as solvent is shown in FIG. 15. The 7.5% PVP granulation with the hydrochloric solvent exhibited greater compressibility than the 7.5% formulation with the MWSF. At equivalent concentration of in-situ binder the MWSF with water granulation was comparable in compressibility to the PVP with hydroalcoholic solvent as can be seen again in FIG. 15.

Figure 16:
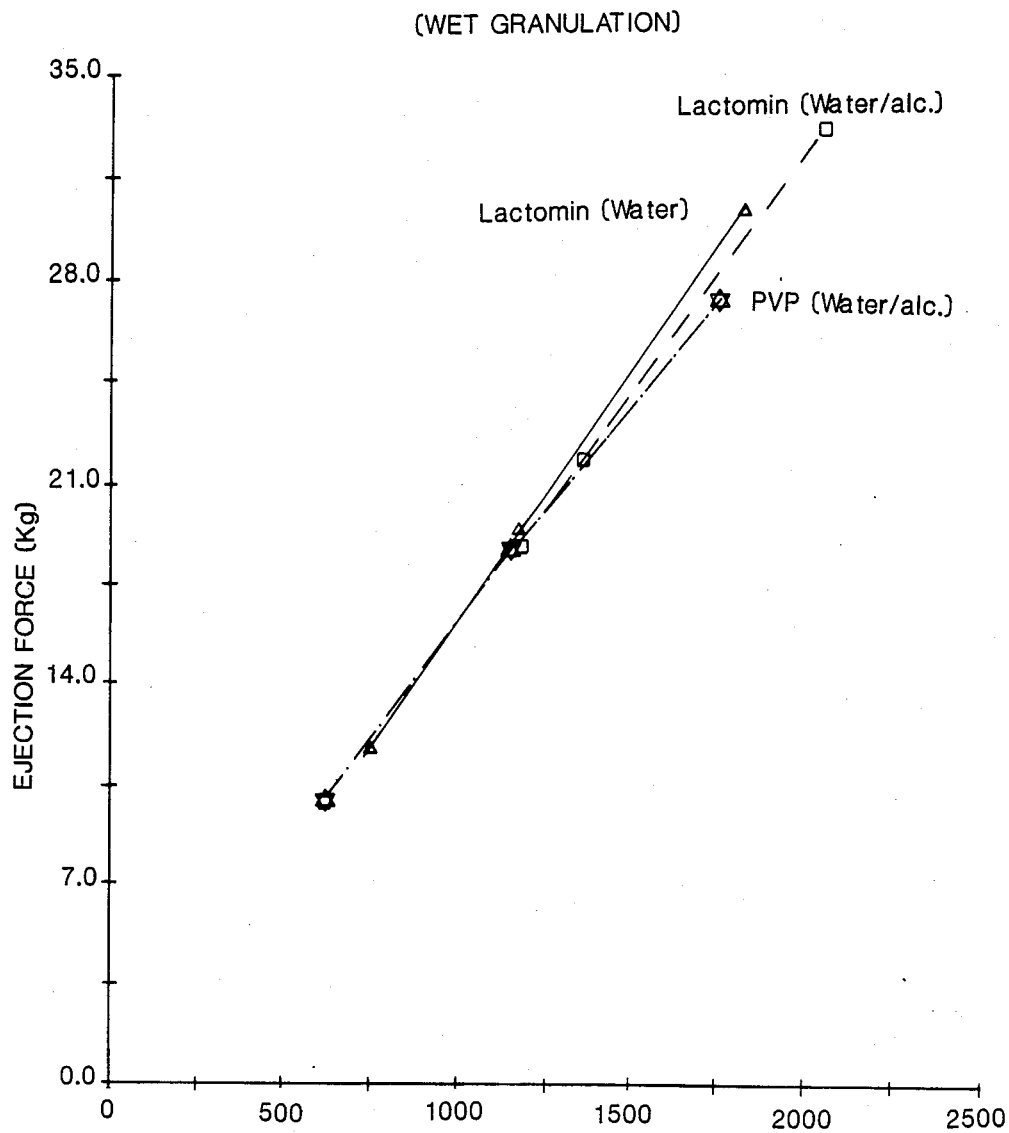
FIG. 16 shows the compression/ejection forces of the material illustrated in FIG. 15.

With the hydroalcoholic based formulations the amount of solvent needed for MWSF was about 250 ml. and 175 ml. for PVP, while MWSF also needed a slightly higher blending time of 35 to 40 minutes compared to 20 minutes for PVP to form acceptable granules. The ejection forces for these formulations were identical as seen in FIG. 16.

In spite of being a good binder, MWSF surprisingly does not adversely affect the disintegration of tablets made from this material as seen in the disintegration data shown in Table 5.

TABLE 5

| DISINTEGRATION DATA | | |
|---|---|---|
| | Hardness (kg) | D.T. (min.) |
| 5% MWSF/Water | 6.11 | 0.54 |
| 7.5% MWSF/Water | 6.32 | 1.53 |
| 10.0% MWSF/Water | 8.07 | 1.79 |
| 5% PVP Water | 7.94 | 1.73 |
| 7.5% MWSF/Water/Alcohol | 8.90 | 0.73 |
| 7.5% PVP/Water/Alcohol | 7.43 | 6.66 |

EXAMPLE 6

Product/Composition Analytical Data

The following analytical data typify the compositions of the microcrystalline whey solids fractions suitable for use in the pharmaceutical excipient applications according to the present invention and illustrate the variety of compositions suitable therefor; Lactomin TM 209, 233, and 317 were prepared from sour whey starting materials, while Lactomin TM 601 was prepared from an acid whey starting material. Illustrative analyses (on a product or "as is" basis) are shown in Table 6.

TABLE 6

| PRODUCT DESCRIPTION: 100% NATURAL WHEY ISOLATE | | | | |
|---|---|---|---|---|
| | LACTOMIN 209 | LACTOMIN 233 | LACTOMIN 317 | LACTOMIN 601 (ACID WHEY) |
| Bulk Density (g/cc, tapped) | 0.47 | 0.38 | 0.28 | 0.75 |
| Solubility in Water (g/100 g @ 25 C.) | <5.0 | <5.0 | <5.0 | <5.0 |

TABLE 6-continued

| PRODUCT DESCRIPTION: 100% NATURAL WHEY ISOLATE | | | |
|---|---|---|---|
| | LACTOMIN 209 | LACTOMIN 233 | LACTOMIN 317 | LACTOMIN 601 (ACID WHEY) |
| Proximate Analysis (%): | | | | |
| Moisture | 5.4 | 8.8 | 10.0 | 13.5 |
| Ash | 17.1 | 27.0 | 21.8 | 41.0 |
| Fat | 0.4 | 0.4 | 0.4 | <0.5 |
| Protein | 33.3 | 13.6 | 7.2 | 28.6 |
| Carbohydrate (GC) | 43.9 | 59.0 | 60.7 | 30.4 |
| Carbohydrate Profile (GC, %): | | | | |
| Lactose | 39.3 | 56.4 | 58.6 | 22.1 |
| Galactose | 0.9 | 0.9 | 0.5 | 0.4 |
| Glucose | 0.3 | 0.5 | 0.5 | <0.1 |
| Carboxylic Acids | 3.4 | 1.1 | 1.0 | 7.9 |
| Minerals (%): | | | | |
| Calcium | 4.4 | 6.2 | 4.1 | |
| Phosphorus | 4.1 | 5.5 | 3.8 | |
| Potassium | 1.5 | 2.1 | 2.3 | |
| Magnesium | 0.9 | 1.8 | 1.2 | |
| Sodium | 0.7 | 0.7 | 0.6 | |

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

INDUSTRIAL APPLICABILITY

As can be seen from the preceding description, the present invention is industrially useful in providing a binding agent derived from whey which is useful in applications involving size enlargement, agglomeration, or binding of chemical, food, and especially pharmaceutical materials prepared by wet granulation and direct compression tableting processes, either with or without pregelatinized starch, gums, or other inert binders.

What is claimed is:

1. A solid pharmaceutical composition suitable for oral or rectal administration comprising a compressed unit dosage of a pharmaceutically active ingredient and optionally one or more inert fillers homogeneously dispersed in a pharmaceutically acceptable binder, wherein a major portion of the binder is a microcrystalline solid phase prepared by raising the pH of a dairy whey lactose permeate having a pH below about 7 to a pH between about 8 and 10 to form: (i) a lactose-rich aqueous solute phase capable of being autoclaved for 10-20 minutes at 121° C. and 15 psi to form a clear, light-colored solute having a pH of about 7; and (ii) a microcrystalline solid phase which contains substantially all of the dissolved solids from said solute phase which would form a precipitate upon autoclaving said solid phase; separating the microcrystalline solid phase from the solute phase; and drying the separated microcrystalline solid phase to form a nontoxic, tasteless, odorless, chalky white free-flowing powder.

2. A composition according to claim 1, wherein the active ingredient is a flavoring agent and the resultant tablet is a confectionary.

3. A composition according to claim 2, wherein the resultant tablet is a candy.

4. A composition according to claim 1, wherein the active ingredient is a bakery dough conditioner or modifier and the resultant tablet is a unit dosage form of said ingredient.

5. A composition according to claim 1, wherein the active ingredient is a pharmaceutical.

6. A composition according to claim 1, wherein the active ingredient is a vitamin.

7. A composition according to claim 1, wherein the active ingredient is a dietary mineral supplement.

8. A composition according to claim 1, wherein the microcrystalline solid phase comprises a major portion of generally spherical, partially porous particles about 5-100 microns in diameter.

9. A composition according to claim 8, wherein said particles are agglomerated to form flowable granules.

10. A composition according to claim 8, wherein the particles are typified by the structure shown in FIG. 17.

11. A composition according to claim 8, wherein the microcrystalline solid phase has a density of about 0.2-1.0 g/cc.

12. In a wet granulation process for preparing a tablet by (a) a wet phase process comprising admixing an active ingredient, a wet binder, and a granulation fluid to form a homogeneous wet mass and forming free-flowing granules therefrom, and (b) a dry phase process comprising admixing the resultant granules with a suitable binder and optionally a filler, and forming tablets from the resultant admixture, the improvement which comprises:

employing as at least a major portion of at least one of the wet phase binder in step (a) and the dry phase binder in step (b) a microcrystalline solid phase prepared by raising the pH of a dairy whey lactose permeate having a pH below about 7 to a pH between about 8 and 10 to form: (i) a lactose-rich aqueous solute phase capable of being autoclaved for 10-20 minutes at 121° C. and 15 psi to form a clear, light-colored solute having a pH of about 7; and (ii) a microcrystalline solid phase which contains substantially all of the dissolved solids from said solute phase which would form a precipitate upon autoclaving said solid phase; separating the microcrystalline solid phase from the solute phase; and drying the separated microcrystalline solid phase to form a nontoxic, tasteless, odorless, chalky white free-flowing powder.

13. A process according to claim 12, wherein said microcrystalline solid phase is employed as the wet phase binder in step (a).

14. The product produced according to the process of claim 13.

15. A process according to claim 12, wherein the microcrystalline solid phase is employed as the dry phase binder in step (b).

16. The product produced according to the process of claim 15.

17. A process according to claim 12, wherein the active ingredient is a flavoring agent and the resultant tablet is a confectionery.

18. A process according to claim 17, wherein the resultant tablet is a candy.

19. A process according to claim 12, wherein the active ingredient is a bakery dough conditioner or modifier and the resultant tablet is a unit dosage form of said ingredient.

20. A process according to claim 12, wherein the active ingredient is a pharmaceutical.

21. A process according to claim 20, wherein the active ingredient includes a vitamin.

22. A process according to claim 12, wherein the active ingredient is a dietary mineral supplement.

23. A process according to claim 12, wherein the microcrystalline solid phase comprises a major portion of generally spherical, partially porous particles about 5-100 microns in diameter.

24. A process according to claim 12, wherein said particles are agglomerated to form flowable granules.

25. A process according to claim 12, wherein the particles are typified by the structure shown in FIG. 17.

* * * * *